(12) United States Patent
Wix

(10) Patent No.: US 9,181,155 B2
(45) Date of Patent: Nov. 10, 2015

(54) PROCESS FOR SYNTHESIS OF ALCOHOLS

(71) Applicant: Haldor Topsøe A/S, Kgs. Lyngby (DK)

(72) Inventor: Christian Wix, Nærum (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/376,604

(22) PCT Filed: Oct. 18, 2012

(86) PCT No.: PCT/EP2012/070674
§ 371 (c)(1),
(2) Date: Aug. 4, 2014

(87) PCT Pub. No.: WO2013/120548
PCT Pub. Date: Aug. 22, 2013

(65) Prior Publication Data
US 2015/0045460 A1    Feb. 12, 2015

(30) Foreign Application Priority Data

Feb. 13, 2012   (DK) .................................. 2012 00112

(51) Int. Cl.
*C07C 27/06* (2006.01)
*C07C 29/149* (2006.01)
*C07C 29/151* (2006.01)
*C07C 29/90* (2006.01)
*C07B 41/02* (2006.01)

(52) U.S. Cl.
CPC ............... *C07C 27/06* (2013.01); *C07B 41/02* (2013.01); *C07C 29/149* (2013.01); *C07C 29/1518* (2013.01); *C07C 29/90* (2013.01)

(58) Field of Classification Search
CPC ..................................................... C07C 27/06
See application file for complete search history.

(56) References Cited

U.S. PATENT DOCUMENTS

| | | | | |
|---|---|---|---|---|
| 7,842,844 | B2 * | 11/2010 | Atkins | ............ 568/880 |
| 2011/0046421 | A1 * | 2/2011 | Daniel et al. | .......... 568/885 |

FOREIGN PATENT DOCUMENTS

| | | |
|---|---|---|
| CN | 101218197 A | 7/2008 |
| EP | 1 741 692 A1 | 1/2007 |
| GB | 694 962 A | 7/1953 |
| WO | WO 2004/056731 A2 | 7/2004 |
| WO | WO 2007/066036 A2 | 6/2007 |

* cited by examiner

*Primary Examiner* — Sudhakar Katakam
(74) *Attorney, Agent, or Firm* — Dickstein Shapiro LLP

(57) ABSTRACT

Process for the catalytic production of alcohol products, wherein by-products comprising ketone, aldehyde and ester compounds contained in the alcohol product are subjected to hydrogenation with a hydrogen-containing purge gas.

6 Claims, 1 Drawing Sheet

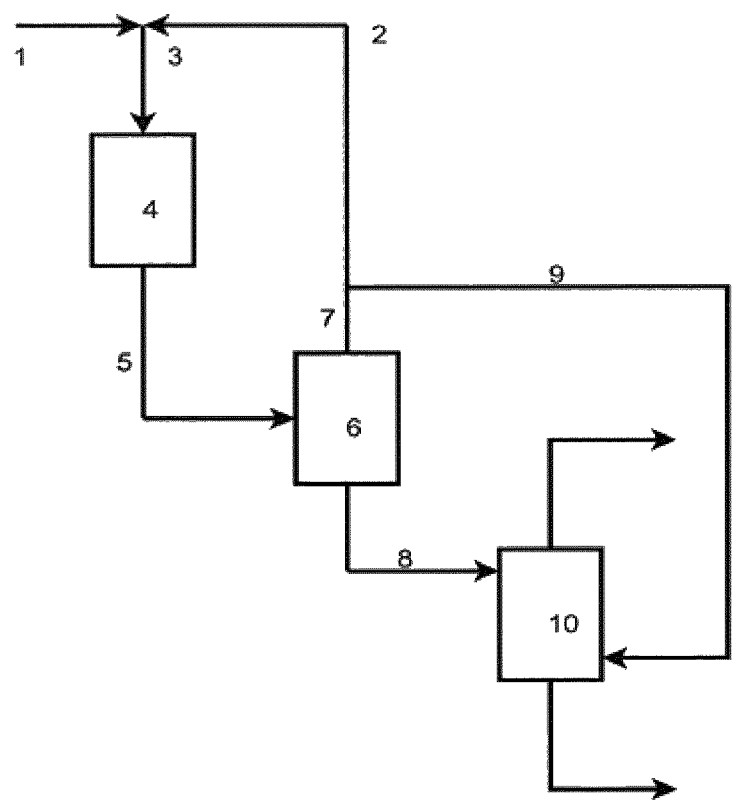

PROCESS FOR SYNTHESIS OF ALCOHOLS

The invention relates to a process for production of alcohols from alcohol synthesis gas. In particular the invention concerns purification of alcohols by conversion of ketones, aldehydes and esters present in the alcohols in presence of one or more catalysts being active in the conversion of ketones, esters, aldehydes and hydrogen to alcohols.

During alcohol synthesis from hydrogen and carbon oxides comprising synthesis gas, by-products such as water, aldehydes, esters and ketones are formed frequently. Species like acetone and methyl ethyl ketone with a boiling point close to that of the prepared alcohol are difficult to remove and consequently the presence of these species will contribute to the demand for a larger and more costly distillation column for the purification of the alcohol product.

It is thus a general object of the invention to provide a process for the production of an alcohol product by catalytic conversion of $H_2$, $CO$ and $CO_2$, wherein the produced alcohol product has a substantially reduced content of oxocompounds including aldehyde and ketone impurities.

Thus, the present invention provides a process for production of alcohol product, comprising the steps of (a) providing an alcohol synthesis gas comprising hydrogen and carbon monoxide;

(b) converting the alcohol synthesis gas into a crude alcohol product stream comprising one or more alcohols and unconverted alcohol synthesis gas in presence of one or more catalysts active in converting the alcohol synthesis gas into the one or more alcohols;

(c) cooling and separating the crude alcohol product withdrawn from step (b) into a gas phase comprising hydrogen, carbon monoxide and carbon dioxide and into a liquid product comprising the one or more alcohols and by-products comprising ketones, esters and aldehydes formed in the conversion of the alcohol synthesis gas;

(d) purging a part of the gas phase obtained in step (c) and recycling the remaining gas phase to step (a);

(e) prior to introduction of the remaining gas phase into step (a) mixing the recycled remaining gas phase product with fresh synthesis gas to form the alcohol synthesis gas; and (f) subsequent to the cooling and separation in step (c) withdrawing the liquid phase and subjecting the liquid phase to a two phase catalytic hydrogenation of the ketones, esters and aldehydes by-products to corresponding alcohols, wherein the liquid phase is hydrogenated with the part of the gas phase being purged from step (d).

Catalysts for use in the alcohol synthesis and hydrogenation ketones, esters and aldehydes are known per se in the art.

On a Cu-based catalyst, alcohol is produced from synthesis gas via the following reactions

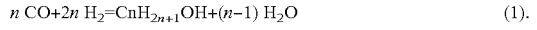
$n\ CO + 2n\ H_2 = CnH_{2n+1}OH + (n-1)\ H_2O$ \quad (1).

The oxo-compound by-products such as acetone and methyl-ethyl ketone etc are formed in small quantities during alcohol synthesis.

Hydrogenation of these by-products is possible on copper, nickel and/or noble metal based catalysts and follows e.g the reactions:

Methyl formate: 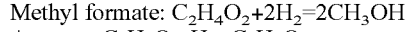$C_2H_4O_2 + 2H_2 = 2CH_3OH$

Acetone: 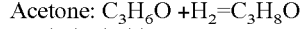$C_3H_6O + H_2 = C_3H_8O$

Methyl ethyl ketone: 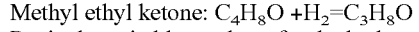$C_4H_8O + H_2 = C_3H_8O$

Particular suitable catalysts for the hydrogenation contain noble metal including Pt and Pd. Base metal catalysts like a 10 wt % Ni—Cu catalyst have been mentioned in the art. E.g. U.S. Pat. No. 5,243,095 discloses a Cu, Fe, Mn, Al based catalyst for ketone hydrogenation and U.S. Pat. No. 3,925,490 claims a Cu, Cr catalyst.

In general, the Cu content in the Cu-containing hydrogenation catalysts is in the range of 10-95% by weight, preferably 40-70% by weight.

The catalyst can be in form of pellets, extrudates or powder.

FIG. 1 of the drawings shows a simplified flow sheet of a process according to an embodiment of the invention. Referring to FIG. 1, alcohol synthesis gas is formed by mixing fresh synthesis gas 1 comprising carbon monoxide and hydrogen with recycle gas 2. Thus the formed synthesis gas 3 is introduced into alcohol synthesis reactor system 4.

The crude alcohol product from 5 from the alcohol synthesis reactor system 4 contains methanol, unconverted alcohol synthesis gas and traces of ketones, esters and aldehydes.

The crude alcohol product 5 is cooled (not shown). The cooled product is then separated in the separator into a vapour and liquid phase, 7 and 8 respectively. A part of the gas phase is purged through line 9 to reduce the amount of inerts accumulating in the synthesis loop (eg. Ar, N2 and CH4). The remainder of the gas forms recycle gas stream 2.

The liquid stream 8 is passed into two phase hydrogenation reactor 10. Ketones, aldehydes and esters contained in the liquid phase 8, are hydrogenated with purge gas 9 into alcohol in presence of a hydrogenation catalyst.

The invention claimed is:

1. A process for production of alcohol product, comprising the steps of:

(a) providing an alcohol synthesis gas comprising hydrogen and carbon monoxide;

(b) converting the alcohol synthesis gas into a crude alcohol product stream comprising one or more alcohols and unconverted alcohol synthesis gas in presence of one or more catalysts active in converting the alcohol synthesis gas into the one or more alcohols;

(c) cooling and separating the crude alcohol product withdrawn from step (b) into a gas phase comprising hydrogen, carbon monoxide and carbon dioxide and into a liquid product comprising the one or more alcohols and by-products comprising ketones, esters and/or aldehydes formed in the conversion of the alcohol synthesis gas;

(d) purging a part of the gas phase obtained in step (c) and recycling the remaining gas phase to step (a);

(e) prior to introduction of the remaining gas phase into step (a) mixing the recycled remaining gas phase product with fresh synthesis gas to farm the alcohol synthesis gas; and (f) subsequent to the cooling and separation in step (c), withdrawing the liquid phase and subjecting the liquid phase to a two phase catalytic hydrogenation of the ketones, esters and/or aldehydes in the by-products to corresponding alcohols, wherein the liquid phase is hydrogenated with the part of the gas phase being purged from step (d).

2. Process according to claim 1, wherein the hydrogenation catalyst is a Cu based catalyst.

3. Process according to claim 2, wherein the Cu content of the hydrogenation catalyst is in the range of 10-95% by weight.

4. Process according to claim 1, wherein the hydrogenation catalyst is a noble metal based catalyst.

5. Process according to claim 1, wherein the hydrogenation of the crude alcohol is performed at a pressure of between 2 and 15 MPa and a temperature between 20° C. and 120° C.

6. Process according to claim 2, wherein the Cu content of the hydrogenation catalyst is in the range of 40-70% by weight.

* * * * *